United States Patent
Hyun et al.

(10) Patent No.: US 10,292,908 B2
(45) Date of Patent: May 21, 2019

(54) NEONATAL ENTERAL FEEDING SYSTEM

(71) Applicant: MEDELA HOLDING AG, Baar (CH)

(72) Inventors: Dongchul D. Hyun, Brea, CA (US); Michael T. Fleury, Brea, CA (US)

(73) Assignee: MEDELA HOLDING AG, Baar (CH)

( * ) Notice: Subject to any disclaimer, the term of this patent is extended or adjusted under 35 U.S.C. 154(b) by 624 days.

(21) Appl. No.: 14/809,868

(22) Filed: Jul. 27, 2015

(65) Prior Publication Data

US 2016/0030292 A1 Feb. 4, 2016

Related U.S. Application Data

(60) Provisional application No. 62/032,392, filed on Aug. 1, 2014.

(51) Int. Cl.
| | |
|---|---|
| *A61M 31/00* | (2006.01) |
| *A61F 7/12* | (2006.01) |
| *A61J 15/00* | (2006.01) |
| *A61M 5/142* | (2006.01) |

(Continued)

(52) U.S. Cl.
CPC ........... *A61J 15/0076* (2015.05); *A23L 33/40* (2016.08); *A61M 5/14232* (2013.01); *A61M 5/14236* (2013.01); *A61J 9/00* (2013.01); *A61J 15/0003* (2013.01); *A61J 2200/40* (2013.01); *A61J 2200/76* (2013.01)

(58) Field of Classification Search
CPC ... A23L 33/40; A61J 15/0003; A61J 15/0076; A61J 2200/40; A61J 2200/76; A61J 9/00; A61M 5/14232
USPC ........................................................ 604/516
See application file for complete search history.

(56) References Cited

U.S. PATENT DOCUMENTS

| | | |
|---|---|---|
| 3,371,975 A | 3/1968 | Meltzer |
| 4,162,855 A | 7/1979 | Bender |
| 4,532,414 A | 7/1985 | Shah et al. |

(Continued)

FOREIGN PATENT DOCUMENTS

| | | |
|---|---|---|
| CN | 201139844 | 10/2008 |
| CN | 201814947 | 5/2011 |
| WO | WO2012174315 | 12/2012 |

OTHER PUBLICATIONS

International Search Report and Written Opinion for International Application No. PCT/US2015/042508; dated Dec. 22, 2015; 14 pages.

(Continued)

*Primary Examiner* — Jason E Flick
(74) *Attorney, Agent, or Firm* — Stetina Brunda Garred and Brucker (57) ABSTRACT

A neonatal enteral feeding system for delivering neonate fluid is disclosed. The system includes a cooling unit for cooling the breast milk before, during and after a feeding cycle to mitigate unwanted bacterial growth and reduction of fat content in the breast milk. The system also includes a warming unit for heating the cold breast milk to a temperature above room temperature (preferably, standard body temperature) so that the neonate can focus his or her energy on healing, growth and digestion instead of heat generation. Additionally, the system has a peristaltic pump which draws the breast milk from a bottom side of the container and the container is vented so as to be capable of delivering all of the breast milk in the container to the neonate.

20 Claims, 6 Drawing Sheets

(51) Int. Cl.
 *A23L 33/00* (2016.01)
 *A61J 9/00* (2006.01)

(56) References Cited

U.S. PATENT DOCUMENTS

| | | | |
|---|---|---|---|
| 5,250,032 | A | 10/1993 | Carter, Jr. et al. |
| 6,033,367 | A | 3/2000 | Goldfield |
| 7,158,719 | B2 | 1/2007 | Cassidy |
| 7,799,008 | B2 | 8/2010 | Hendricks |
| 8,052,656 | B2 | 11/2011 | Dorsey |
| 8,663,161 | B2 | 3/2014 | Hyun et al. |
| 2004/0073161 | A1 | 4/2004 | Tachibana |
| 2004/0140304 | A1* | 7/2004 | Leyendecker ...... A47J 36/2433 219/386 |
| 2005/0008354 | A1 | 1/2005 | Cassidy |
| 2005/0209563 | A1 | 9/2005 | Hopping et al. |
| 2007/0017229 | A1 | 1/2007 | Shim |
| 2007/0118078 | A1 | 5/2007 | McNally et al. |
| 2008/0075819 | A1 | 3/2008 | Hartmann et al. |
| 2008/0119782 | A1 | 5/2008 | Steinman et al. |
| 2008/0262409 | A1 | 10/2008 | Derrico |
| 2010/0326285 | A1 | 12/2010 | Kang |
| 2012/0271271 | A1 | 10/2012 | Hyun et al. |
| 2012/0283690 | A1 | 11/2012 | Knight |
| 2013/0237957 | A1 | 9/2013 | Hyun et al. |
| 2014/0207063 | A1 | 7/2014 | Hyun et al. |
| 2014/0242213 | A1* | 8/2014 | McCarty ............ A61J 9/00 426/2 |

OTHER PUBLICATIONS

International Search Report and Written Opinion for International Application No. PCT/US2014/048079; dated Nov. 18, 2014; 14 pages.

www.zawya.com; "GE Healthcare's New Transportable Power Source Showcased at Arab Health Strengthens Neonatal Care"; Jan. 28, 2011; 4 pages.

www.ncbi.nlm.nih.gov; "Effect of Enteral Feeding Temperature on Feeding Tolerance in Preterm Infants"; Dec. 31, 2010; 1 page.

Paragon Medical; "Fluid Warmers"; Feb. 10, 2011; 3 pages.

* cited by examiner

NEONATAL ENTERAL FEEDING SYSTEM

CROSS-REFERENCE TO RELATED APPLICATIONS

This application claims the benefit of U.S. Provisional Patent Application Ser. No. 62/032,392, filed Aug. 1, 2014, which is wholly incorporated by reference in its entirety herein.

STATEMENT RE: FEDERALLY SPONSORED RESEARCH/DEVELOPMENT

Not Applicable

BACKGROUND

The embodiments disclosed herein relate to systems and methods for feeding a preterm infant or neonate. More particularly, the disclosed systems and methods relate to improvements in maintaining the fat content and nutritional level of breast milk used in feeding preterm infants. Also, the disclosed systems and methods relate to delivery of all of the nutritional fluid (e.g., breast milk or formula) without delivery of air to the preterm infant/neonate.

Nutritional delivery to a preterm infant or enteral feeding is an important part of caring for the preterm infant in neonatal intensive care units. Typically, the preterm infant is fed with a feeding tube that delivers breast milk or neonatal formula directly into the stomach of the preterm infant. The feeding tube is generally introduced either through the nose (i.e., nasally) or through the mouth (i.e., orally). When breast milk is used as the nutritional fluid, it is typically obtained from the mother, or a donor, via a conventional breast pump and stored within a container. The container is then typically placed in a refrigerator or freezer for storage. Subsequently, when it is desired to feed the neonate, the breast milk is typically transferred from the container into a syringe for use in a conventional syringe pump, or alternatively, placed in a gravity feeding container and subsequently delivered to the neonate via the feeding tube. It has been reported, however, that the fat percentage of breast milk may be reduced every time it is transferred from one container to another. Further, it has been suggested that the fat content in milk may be higher in refrigerated milk than in non-refrigerated milk. In addition, it is known that bacteria may grow more rapidly in non-refrigerated milk compared to refrigerated milk. Additionally, studies have shown that preterm infants respond favorably when the nutritional liquid (e.g., breast milk or neonatal formula) is closer to standard body temperature (i.e., 98.6° F.) when digested by the preterm infant. When the nutritional liquid is provided to the preterm infant closer to standard body temperature, the preterm infant was found to digest more of the nutritional liquid. Moreover, other studies have found that the lower the body temperature of the preterm infant, the higher the likelihood of mortality of the preterm infant. As such, it is important to preserve the preterm infant's energy so that the preterm infant does not need to divert energy away from healing and growth to generate heat.

Prior art devices for feeding preterm infants have been introduced into the marketplace. However, these devices typically do not address the refrigeration and/or heating aspects desirable for the storage of breast milk and its preferred use as a nutritional fluid at body temperature. Further, other prior art devices have been introduced for warming nutritional liquid (e.g., breast milk or neonate formula) provided to pre-term infants. For example, U.S. Pat. No. 8,663,161 and U.S. patent application Ser. No. 14/222,832 (the entireties of which are herein incorporated by reference) disclose devices for heating nutritional fluids for use in feeding preterm infants.

Accordingly, there is a need in the art for improved methods and systems for feeding preterm infants in a manner that maximizes the fat content and nutritional aspect of breast milk, by keeping the breast milk refrigerated until administration to the infant, and by heating the breast milk to body temperature shortly before delivery to the infant.

BRIEF SUMMARY

The embodiments discussed herein address the needs discussed above, discussed below and those that are known in the art.

A neonatal enteral feeding system is disclosed herein. The system uses a container with nutritional fluid (e.g., breast milk or neonatal formula) which is loaded into the system for dispensing the nutritional fluid to neonatal infant through oral or nasal feeding tubes. The container may be a standard breast milk container, or any other suitable container for retaining the breast milk during use. The system has a cooling unit for actively keeping the milk cold before, during and after a feeding cycle. Additionally, the cooling unit of the system allows for a caregiver to insert the container with breast milk into the system at a time prior to beginning the feeding and programming the system to feed the preterm infant at a later time. This prevents feeding delays in the event that the medical professional cannot manually start a feeding cycle at that particular time. During the interim period, the cooling unit keeps the breast milk refrigerated until feeding begins.

By way of example and not limitation, the system may include a delayed start timer, such that when the caregiver inserts the breast milk container into the system, the caregiver may select a desired start feed time. The cooling unit is turned on and maintains the breast milk in the container in a refrigerated state at least until the feed time which is initiated without user intervention (i.e., automatically). Alternatively, the breast milk container may be kept cooled in the system with the cooling feature while waiting for the proper feeding time and feeding may be manually initiated at a later time by a medical professional (e.g., nurse). While it is envisioned that the milk may be kept in the same container it is collected in, various other containers may be utilized in the system and are expressly contemplated herein. The system keeps the breast milk cold after removal from a refrigerator and throughout long-term feeding cycles, thereby reducing bacterial growth. The system then pumps the milk through tubing and preferably warms the milk to standard body temperature shortly before being introduced into the neonate's stomach. It is envisioned that by reducing the loss of milk fat from transferring containers and uncooled milk, the present system allows for a more nutritious enteral feeding for distressed neonates and helps to focus the preterm infant's energy on growth and healing.

One embodiment of the present disclosure envisions a neonatal enteral feeding system having a breast milk container, a cooling unit, a pump, a tube, and a warming unit. The cooling unit may be capable of receiving and cooling the breast milk container. However, it is also contemplated that the cooling unit may be alternatively configured. For example, the cooling unit may interface with or extend from a cap of the container to draw heat through the cap or provide cooling from the cap instead of cooling the container. In this instance, the cap may receive the cooling unit such as a gel coolant. The tube may be in fluid connection with both the container and a stomach of the neonate. To deliver the breast milk to the neonate, the tube may be routed through the pump and the warming unit. The pump draws breast milk out of the container. The warming unit provides warm milk to the preterm infant. The warming unit is preferably attached inline to the pump tubing proximal to the neonate and is capable of warming breast milk to a desired temperature before administration to the neonate.

As discussed, in one embodiment the container may optionally be a standard container capable of being used with a breast pump. It is envisioned that different container types may be utilized, for example, syringes, gravity feed bags or containers, and the like. Further, the container may utilize a removable cap with a venting mechanism to allow for the equalization of atmospheric pressure inside the container so that a vacuum is not created within the container, and the entire volume of milk in the container may be fully dispensed. One embodiment of the venting mechanism includes a vent straw fitted with a hydrophobic filter. Various other venting mechanisms are contemplated herein including but not limited to the use of a valve in place of a hydrophobic filter, filter vents or valves located directly within the cap, hydrophobic filters positioned between the container and the cap, filter vents or valves located directly within the container or between the container and the cap rather than the cap, and other venting mechanisms known within the art. The pump cap further may include a mating connector in fluid connection with the pump cap and the pump tubing to connect the pump tubing to the container.

The cooling unit can include one or more cooling modules, and may take various forms and be implemented in various configurations. For example, in one embodiment the cooling module may be made up of two separable cooling jackets (i.e., cold sinks) capable of surrounding the container. Other methods of cooling the breast milk container may be utilized, such as integrating a cooling element into the container itself and/or the container cap. In an exemplary embodiment, each cooling jacket is part of a cooling module which may have a Peltier thermoelectric cooler disposed between the cold sink/cooling jacket and a heat sink. However, it is contemplated that various other conventional cooling systems may be utilized, for example, vapor-compression refrigeration, evaporative cooling, or cold gel packs. Further, the cooling modules of the cooling unit may be traversable in relation to each other between opened and closed positions to allow for easy insertion, removal, and retention of the container within the cooling unit. In order to traverse the cooling modules, each cooling module may be attached to a common axle having two different threads with different thread orientations. The common axle may be attached to an actuator, preferably a stepper motor. Alternatively, various method of adjusting the cooling jackets may be utilized, including manual methods (e.g., crank) and various manual slide and clamp mechanisms. At least one condensation air tube may be used to blow air over the container and cooling jackets to prevent a buildup of condensation. Other moisture removal mechanisms are also contemplated such as a ring shaped sponge disposed around the container or cap.

The pump may take various forms, including a positive displacement pump such as a peristaltic pump. When a peristaltic pump is used, the pump tubing may include a peristaltic section of tubing that is more compliant than the rest of the pump tubing, to allow for ease of use with the rollers of the pump. Furthermore, the pump may be physically attached to or contained within a body of the system. The system may further include an input device, such as a keypad, for example and a display. In certain embodiments, the input device and display may be combined as a unitary touchscreen. Various aspects of the feeding cycle may be controlled by the input device, such as the rate of delivery, delayed start time of feeding, on and off cycles of feeding, and the like.

The system may further include a milk level monitoring device. For example, the milk level monitoring device may be a rotary encoder on the motor, a camera vision system, an LED monitoring system, a laser monitoring system, or utilize other known liquid measuring techniques. The system may further include an agitation component, to mix or agitate the milk within the container to minimize fat loss. The agitation component may be, for example, a rotary-sealed propeller located in the lid of the breast milk container, a rotating magnetic device located in the pumping unit in combination with embedded magnets placed within the container, an ultrasonic transducer, or utilize other known liquid agitating techniques.

Another embodiment of the present disclosure envisions methods of feeding a preterm infant/neonate. In one method, breast milk obtained from the mother of the neonate or from donor sources is cooled below body and/or room temperature in a delivery container. The delivery container may be, but is not necessarily, a breast milk container. The cooled breast milk is pumped out of the delivery container and through a tube in fluid connection with the neonate's stomach. Within the tubing, the breast milk is heated prior to delivery of the breast milk to the neonate. The breast milk is heated above room temperature, and in certain embodiments, is preferably heated to approximately the infant's body temperature.

In relation to the system described herein, the delivery container may be inserted into a cooling module capable of maintaining the breast milk at a temperature below room temperature, wherein the container is fluidly connected to a feeding tube of the neonate via pump tubing. The pump tubing is routed through a pump and through a warming unit capable of warming the breast milk to a temperature above room temperature. The breast milk is then pumped into the feeding tube which is disposed in the neonate, thereby feeding the neonate.

The combination of components described herein allows for significantly improved feeding methods. For example, through the use of a peristaltic pump (or other positive displacement pumps) and the venting mechanism in the container and/or cap, it is possible to deliver the entirety of the breast milk in the system to the neonate without delivering excess air. In contrast to a syringe pump, the peristaltic pump may continue to run after all of the breast milk has exited the container, thereby delivering the remaining breast milk contained within the tubing to the neonate. Also, a peristaltic pump provides a consistent flow rate of the nutritional liquid through the tubing. The venting mechanism allows for this continued feeding without the formation of a vacuum within the container. Additionally, by utilizing the milk level monitoring device, it is possible to fully deliver the entirety of the breast milk to the neonate without delivering excessive amounts of air. In this respect, depending on the level monitoring device utilized, the system is capable of sensing when the container and/or tubing is empty, and in conjunction with the pumping unit's programming, the feeding cycle may be stopped at the appropriate time to prevent delivery of excess air to the neonate. Further, the integrated cooling unit, or mechanism allows for breast milk to be stored directly in the system for prolonged periods of time with a reduced risk of bacterial growth or reduced nutritional content of the milk. For example, the cooling mechanism may allow for extended feeding times, which may be beneficial in certain cases. Additionally, the cooling mechanism allows for preset delayed feeding times, wherein the milk container is inserted into the system prior to feeding at a later time by use of the delayed start timer. The various features discussed herein alone and in combination with each also facilitates the portability of the system.

The above mentioned features of the preferred embodiments and variants of the invention described herein and in the claims may be combined with each other thereby forming additional preferred embodiments.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Referring now to the drawings, a system 10 for feeding a preterm infant breast milk is shown. The system 10 may comprise a cooling unit 12 for maintaining breast milk contained in a container 14 in a cold state before, during and after feeding of the preterm infant to mitigate bacteria growth and reduction of fat content in the breast milk. Additionally, the system 10 may include a peristaltic pump 16 which in conjunction with a venting mechanism of the container 14 allows the system 10 to dispense all of the breast milk contained in the container 14 without delivering excessive air to the preterm infant during feeding. Breast milk is the optimal food especially for preterm infants who may already be struggling for life. The system 10 helps to prevent waste of beneficial breast milk. The system 10 may also include a breast milk warming unit 18 for raising the temperature of the breast milk which is kept in a cold state by the cooling unit 12 so that the preterm infant receives the breast milk at a standard body temperature to help focus the preterm infant's energy on healing and growth with the digestion of the warmed breast milk, not regulating his/her temperature due to consumption of cold breast milk.

Figure 4:
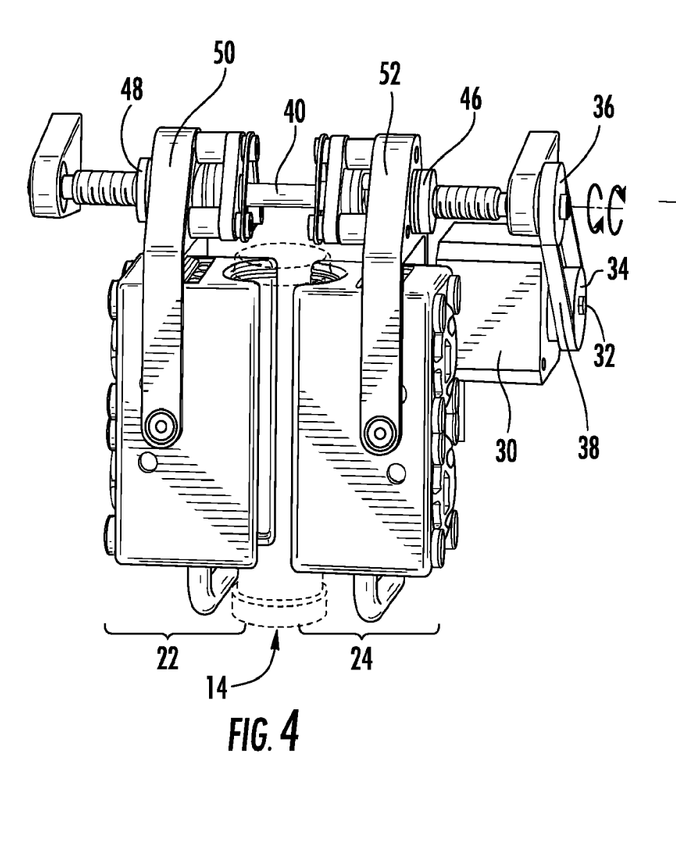
FIG. 4 is a front perspective view of a cooling unit with first and second cooling modules in a closed position.
Figure 5:
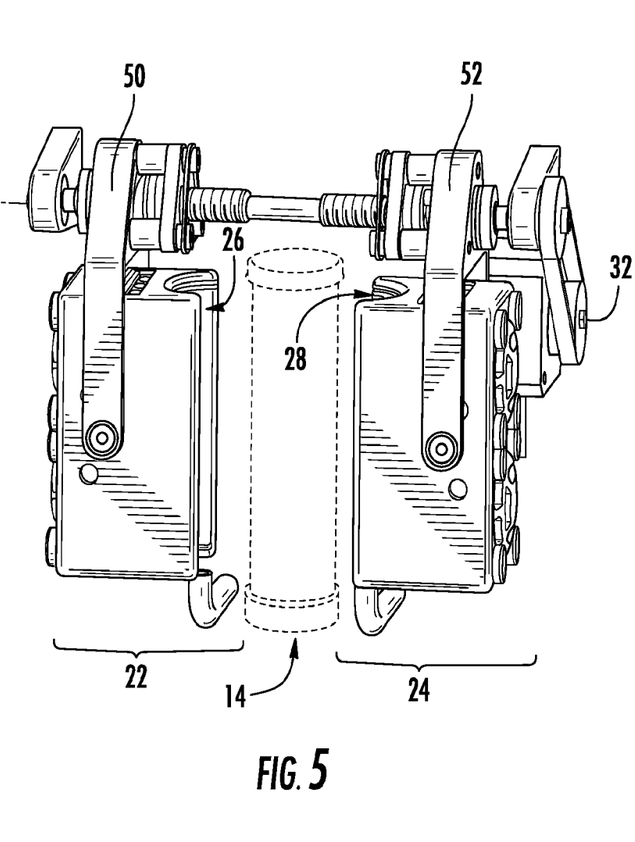
FIG. 5 is a rear perspective view of the cooling unit shown in FIG. 4 with the first and second cooling modules in an opened position.

Referring now to FIGS. 1, 2, 4, 5 and 8, the cooling unit 12 may be incorporated into a body 20 of the system 10. The cooling unit 12 may have first and second modules 22, 24. The first and second modules 22, 24 may be traversed between a closed position as shown in FIG. 4 and an opened position as shown in FIG. 5. In the opened position, the container 14 may be inserted or removed from between cold sinks 26, 28 (or cooling jackets) of the first and second modules 22, 24. In the closed position, the cold sinks 26, 28 may contact the exterior surface 56 of the container 14 to hold the container 14 in place between the first and second modules 22, 24 so as to serve as a holding mechanism. To remove the container 14 from the cooling unit 12, the first and second modules 22, 24 are traversed toward the opened position as shown in FIG. 5 to release the container 14.

Referring to FIGS. 4 and 5, the first and second modules are traversable between the opened and closed positions with the use of a suitable device, such as, for example, a motor 30. Preferably, the motor 30 is a stepper motor so that the positions of the first and second modules 22, 24 may be determined by the amount of rotation of the output shaft 32 of the stepper motor 30. The stepper motor 30 may have a first sprocket 34 which is connected to a second sprocket 36 with a timing belt 38. The second sprocket 36 is mounted to a common axle 40 having first and second threads 42, 44. The first and second threads 42, 44 may respectively be left-handed threads and right-handed threads or vice versa. Matching nuts 46, 48 may be threadably engaged to the first and second threads 42, 44. The matching nuts 46, 48 are fixedly attached to the first and second modules 22, 24 of the cooling unit 12 with attachment fixtures 50, 52. When the stepper motor 30 rotates the output shaft 32 in a first direction about its longitudinal axis, the axle 40 is rotated which in turn traverses the first and second modules 22, 24 toward the closed position or the open position. To traverse the first and second modules 22, 24 toward the open position or the closed position (i.e., opposite direction), the stepper motor reverses rotation of the output shaft 32.

In lieu of the motor 30, the common axle 40 may be rotated with a hand crank that extends out of the body 20 of the system 10. In addition, other clamping/mounting devices are contemplated.

Figure 7:
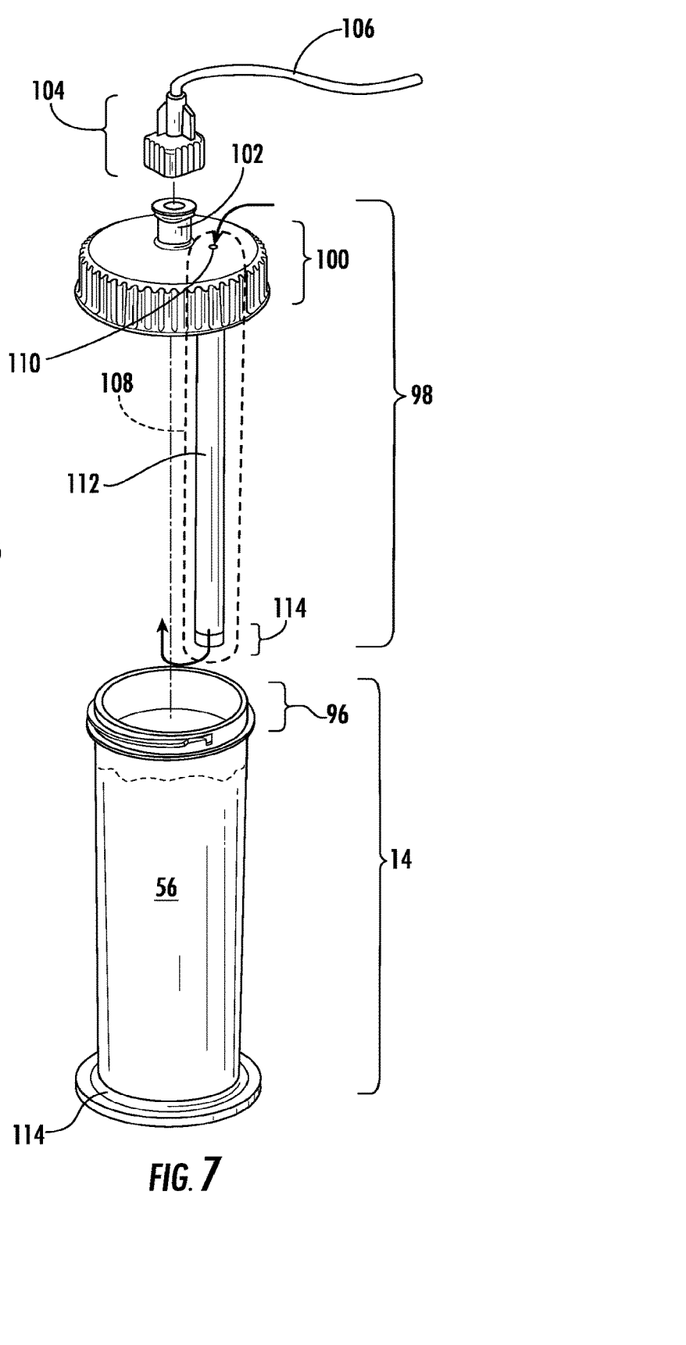
FIG. 7 is an exploded perspective view of a common breast milk collection container and a cap with a venting mechanism and an output port for use with the system shown in FIG. 1.
Figure 8:
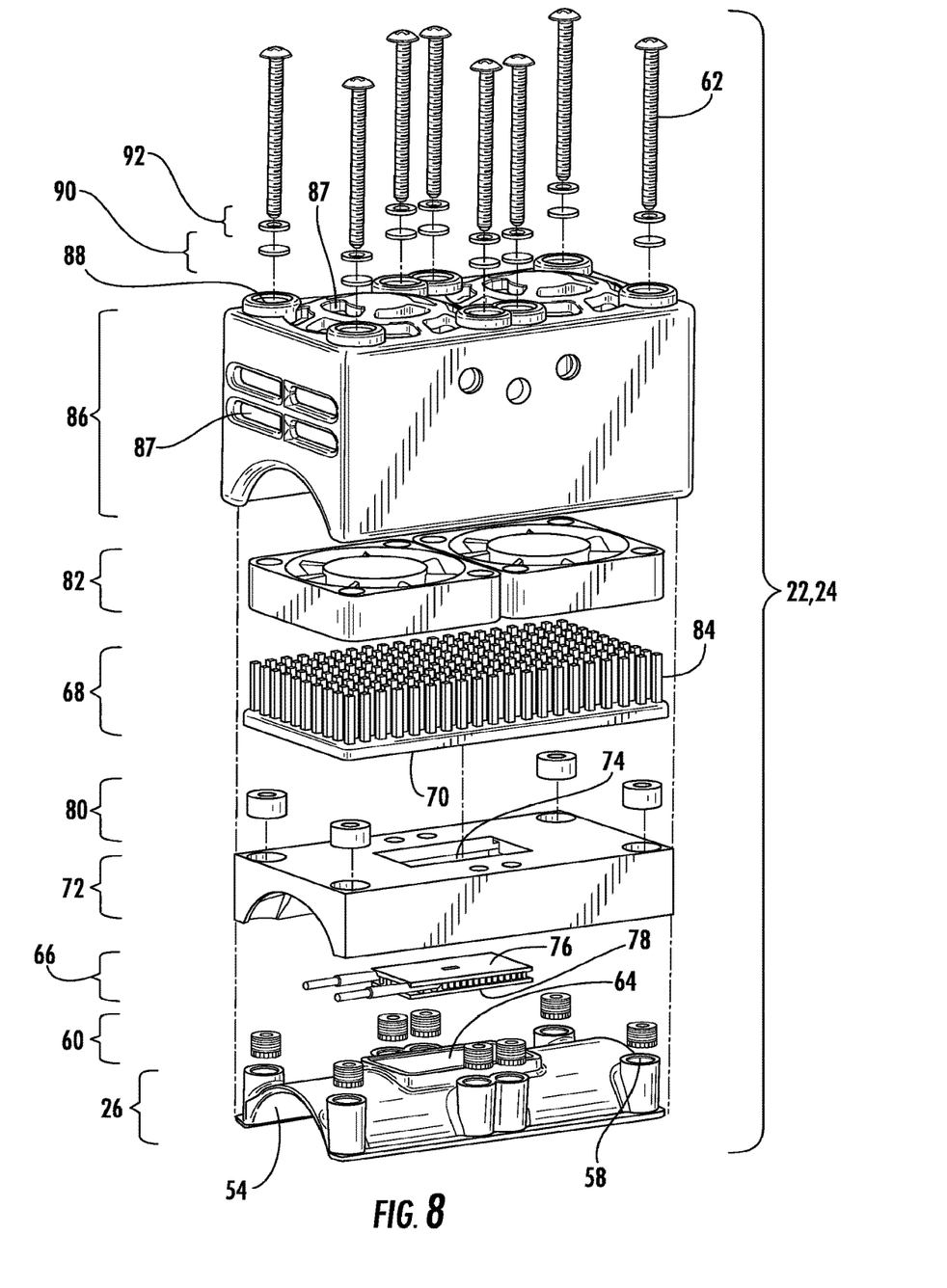
FIG. 8 is an exploded perspective view of one of the first and second cooling modules of the cooling unit.

Referring now to FIG. 8, one of the cooling modules 22, 24 of the cooling unit is shown. The other cooling module 22, 24 may be identical to the one shown in FIG. 8 but oriented in the opposite direction, as shown in FIGS. 4 and 5. The cooling module 22, 24 may have the cold sink 26. An interior surface 54 of the cold sink 26 may be sized and configured to match an exterior surface 56 of the container 14 (see FIG. 7). In particular, when the first and second modules 22, 24 are traversed to the closed position, the entire interior surface 54 or a substantial portion of the interior surface of the cold sink 26 of the first and second modules 22, 24 preferably contacts the exterior surface 56 of the container 14 in order to allow maximum conduction of heat out of the breast milk contained in the container 14 through the container 14. For example, 50% or more of the interior surface 54 may contact the exterior surface 56. This allows for control of the temperature of the breast milk while waiting for the start of the feeding cycle, during the feeding cycle and thereafter. The feeding cycle starts when the system 10 starts to flow nutritional liquid to the neonate and ends when the system 10 stops flowing nutritional liquid to the neonate.

It is also contemplated that a clear plastic door covering (not shown) may be disposed in front of the container 14. The door covering may be pivotable between an opened and closed position and may be disposed in front of the container 14 when the first and second module 22, 24 are traversed to the closed position. Alternatively, the door covering may be fixed and cover the frontal area of the cooling unit 12 regardless of whether the first and second modules 22, 24 are at the closed or opened positions. In this alternative embodiment, the container 14 would be inserted and removed from a cooled storage position between the first and second cooling modules 22, 24 from a bottom side of the system.

The cold sink 26 may preferably be fabricated from a material having a high heat transfer coefficient such as aluminum, copper or other material known in the art or developed in the future. The cold sink 26 may be machined or die cast. The cold sink 26 may have recesses 58 for fixedly receiving threaded inserts 60. The threaded inserts 60 receive screws 62 that hold the various components of the first and second modules 22, 24 together. The cold sink 26 may have a flat surface 64 for receiving a thermoelectric cooler 66 (i.e., thermoelectric cooler) which transfers heat away from the cold sink 26 and into the heat sink 68. The flat surface 64 increases surface contact, and thus heat transfer, between the thermoelectric cooler 66 and the cold sink 26. Other equivalent devices in lieu of the thermoelectric cooler 66 are also contemplated such as vapor-compression refrigeration, evaporative cooling and cold gel packs or any other suitable device. Additionally, a lower surface 70 of the heat sink 68 may also have a corresponding flat surface that contacts the thermoelectric cooler 66 to also increase the surface contact and heat transfer coefficient therebetween 68, 66. An insulator 72 may be disposed between the cold sink 26 and the heat sink 68. The insulator 72 may be sized and configured to fit between the space defined by the cold sink 26 and the heat sink 68 and also provide an aperture 74 for allowing the thermoelectric cooler 66 to contact both the lower surface 70 of the heat sink 68 and the flat surface 64 of the cold sink 26. A heat transfer compound may be applied to opposed surfaces 76, 78 of the thermoelectric cooler 66 to increase efficiency of heat transfer between the cold sink 26 and the thermoelectric cooler 66 as well as the thermoelectric cooler 66 and the heat sink 68.

To further increase or maintain a high heat transfer coefficient from the cold sink 26 to the heat sink 68, pressure applied to the opposed surfaces 76, 78 of the thermoelectric cooler 66 by the lower surface 70 of the heat sink 68 and the flat surface 64 of the cold sink 26 may be evenly distributed about the opposed surfaces 76, 78. To aid in evenly distributing the forces, compressible spacers 80 which receive the screws 62 may be used to even the load applied to the opposed surfaces 76, 78 from the lower surface 70 of the heat sink 68 and the flat surface 64 of the cold sink 26. The compressible spacers 80 are preferably fabricated from a suitable polymer material such as rubber. Two fans 82 may be disposed over the heat sink 68 to blow air over the fins 84 of the heat sink 68. However, it is also contemplated that any other suitable arrangement for cooling, including material alterations or physical modifications can be incorporated into the system, as well as one or more fans 82 that may be used to blow air over the fins 84 of the heat sink. A body 86 of the module 22, 24 may encapsulate the thermoelectric cooler 66, insulation 72, spacers 80, heat sink 68 and the fans 82. The body 86 of the module 22, 24 may be fabricated from a strong polymer material. Moreover, the body 86 may have vent holes 87 to allow the fan to move the air across the fins 84 of the heat sink 68. The screws 62 are inserted through apertures 88 of the body 86 and through one or more of the fans 82, heat sink 68, compressible spacers 80, insulation 72 are threaded onto the threaded inserts 60. Pressure on the opposed surfaces 76, 78 can be regulated by tightening and loosening one or more of the screws 62. The screws 62 can be held in place by wave springs 90 and washers 92.

Although the interior surface 54 of the cold sink 26 of the first and second modules 22, 24 are sized and configured to receive the exterior surface 56 of the container 14, it is also contemplated that a gap may exist therebetween. In this instance, the cold sink 26, 28 transfers heat out of the breast milk contained in the container 14 by cooling the air around the container 14 instead of through direct conduction between the container 14 and the cold sink 26. Moreover, the cold sink 26 or a cap capture member may capture the replacement cap 98 or a flange 114 of the container 14 to hold the position of the container 14 in the cooling unit 12.

The thermoelectric cooler 66 may be controlled with a temperature controller 119. The temperature controller 119 may be in electrical communication with the thermoelectric cooler and the power supply 146 through the leads of the thermoelectric cooler 66 in order to increase or decrease the Peltier effect.

Figure 2:
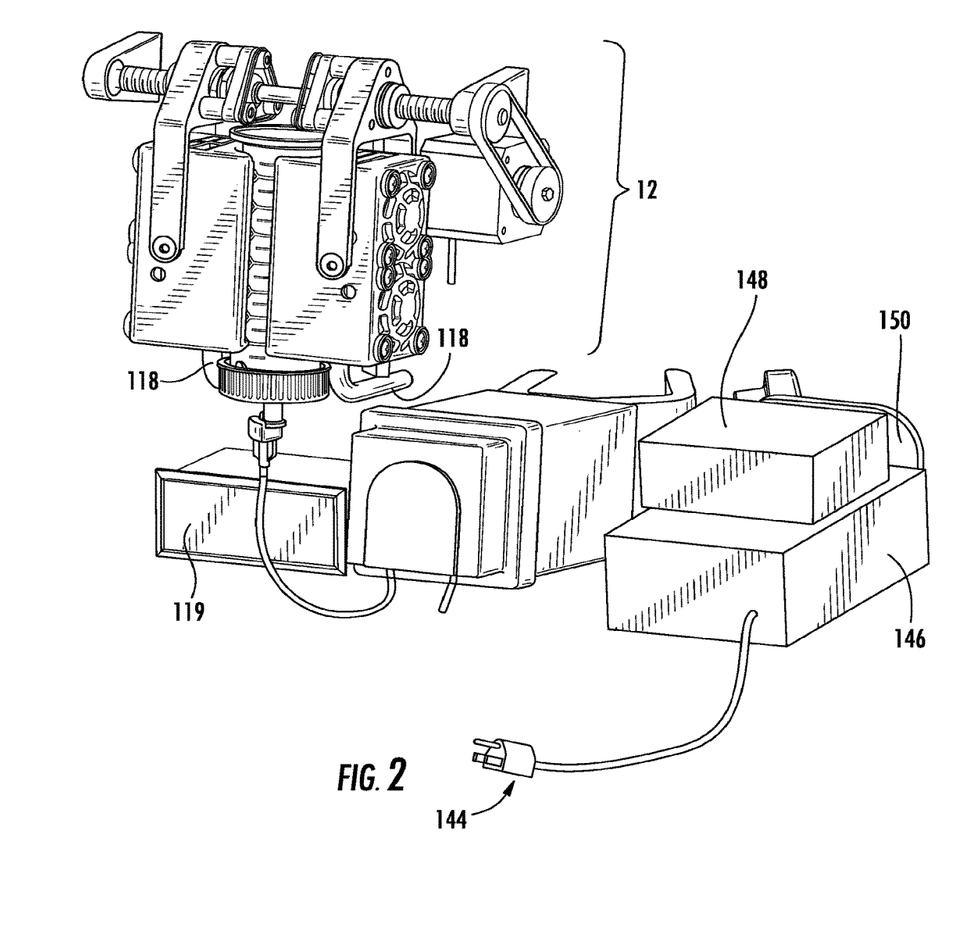
FIG. 2 is a front perspective view of internal components of the system shown in FIG. 1 with the case and other components removed for clarity.
Figure 3:
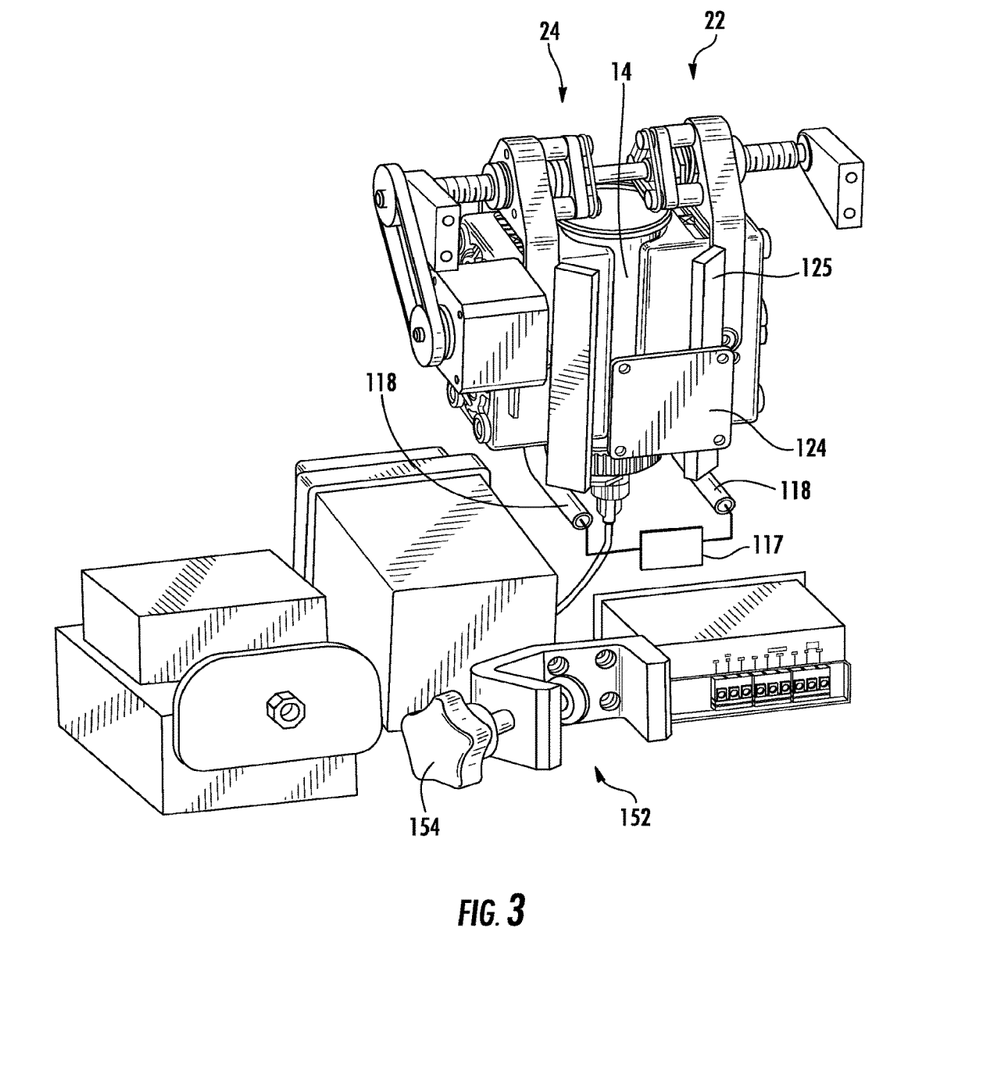
FIG. 3 is a rear perspective view of the internal components shown in FIG. 2.

A condensation reduction/blow-off apparatus 116 may have an air pump 117 which is in fluid communication with air tubes 118, as shown in FIGS. 2 and 3. The open or exhaust end of the air tubes 118 may be directed toward the cooling unit. The open end of the air tubes 118 may be disposed below the cold sink 26 and be operative to blow air over the surface of the container 14 and/or through the vent holes 87 of the body 86 of the first and second modules 22, 24. By blowing air over these components, condensation is mitigated or does not form. Other means of containing and controlling condensation are also contemplated such as a disposable ring shaped sponge placed around the container 14.

The above description of the cooling unit 12 revolved around first and second cooling modules 22, 24 that surround the container 14 about its exterior periphery. However, it is also contemplated that a cooling module may be configured and sized to be disposed within a recess of the container 14 in lieu of or in addition to the first and second cooling modules 22, 24. The recess may be formed in a wall of the container 14 or in the cap 98. Beneficially, by doing so, the external size and configuration may be kept the same while changing the volume size of the container 14. In this way, the system 10 need not be changed to account for different volume containers 14. The container 14 may be a specially designed container 14 used for collecting breast milk with a breast pump and also have the recess for receiving the cooling module.

Figure 6:
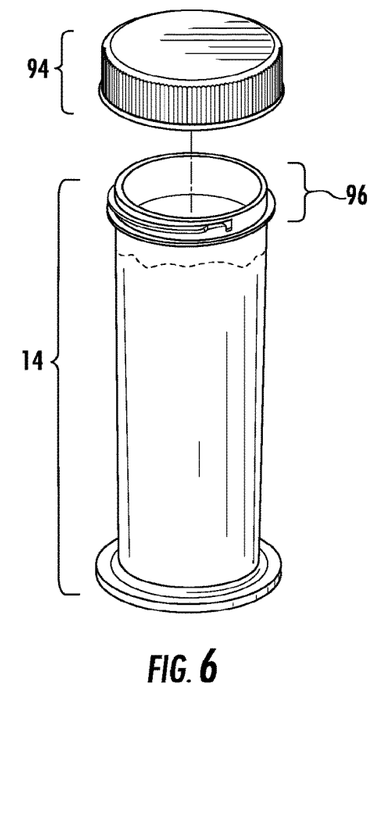
FIG. 6 is an exploded perspective view of a common breast milk collection container and a cap.

Referring now to FIGS. 6 and 7, the container 14 may be a common container used for collecting breast milk with a breast pump. The container 14 defines the exterior surface 56 which typically has a cylindrical configuration. However, it is also contemplated that other external configurations for the container 14 may be employed such as oval and square. The container 14 may also be provided with a cap 94 used to seal off the container 14. When the container 14 is filled with breast milk, threads of the cap 94 are threadably engageable to threads 96 disposed at the open end of the container 14. The cap 94 may be used to seal off the container 14 during storage.

Figure 1:
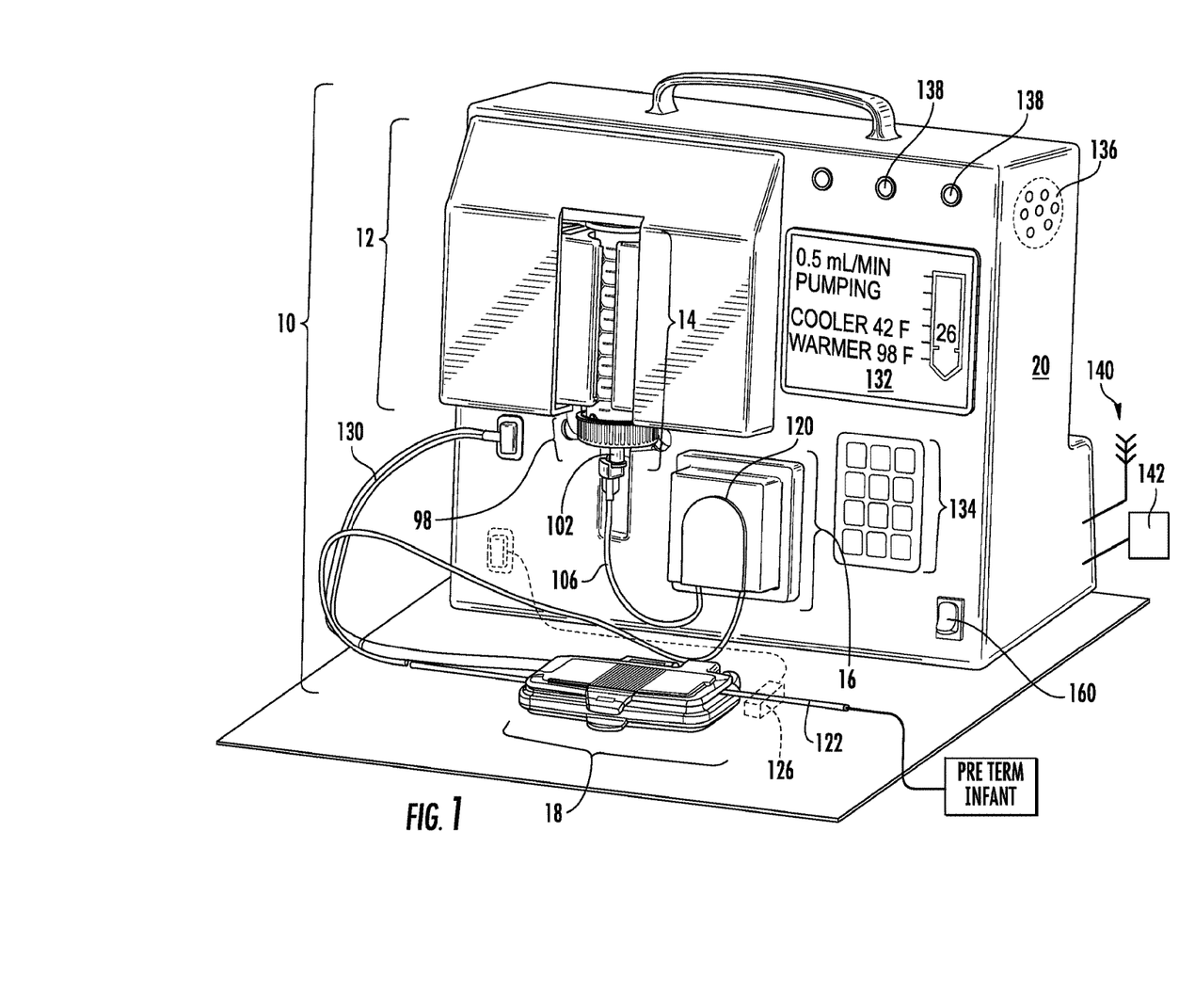
FIG. 1 is a perspective view of a neonatal enteral feeding system.

The system 10 may provide a ventable cap 98. The container 14 and the cap 98 form a liquid holding system. The ventable cap 98 may also have threads formed in a cover component 100 that is threadably engageable to the threads 96 of the container 14. The cover component 100 may also have an output port 102 that can receive a connector 104 fitted onto a first end of an extension tube 106. The breast milk contained within the container 14 flows out of the output port 102 into the extension tube 106 during feeding. During feeding, the container 14 and the replacement cap 98 are inverted from the orientation shown in FIG. 7. The inverted position of the container 14 and the replacement cap 98 is shown in FIG. 1. In the inverted position, as breast milk flows out of the output port 102, air is introduced into the container 14 by way of vent 108 to prevent a vacuum from forming and allowing all of the nutritional fluid to be fed to the neonate. The vent 108 includes a hole 110 in the cover component 100 and a rigid elongate tube 112 that extends to a bottom of the container 14. The tube 112 is sufficiently rigid so long as the tube remains erect when the container 14 and the cap 98 are inverted. When the container 14 and the ventable cap 98 are inverted as shown in FIG. 1, the breast milk flows toward the output port 102 and air is introduced into the upper portion of the inverted container 14. Moreover, optionally, the interior surface of the cover component 100 of the cap 98 may have a conical or concave configuration that leads to the hole 110 so as to drain all of the breast milk out of the container 14 during the feeding cycle. A hydrophobic filter 114 may be fitted at a distal end of the elongate tube 112 to allow air to enter into the container 14 but to prevent breast milk from spilling out of the vent 108 of the container 14 during handling. The distal end of the elongate tube 112 is shown in FIG. 7 as being located at the lower end of the elongate tube 112. The elongate tube 112 assists in introducing the air towards or above the top of the fluid level when the container 14 is inverted during the feeding cycle.

The vent 108 may alternatively be a one-way valve or other structure known in the art or developed in the future for allowing air to enter into the container 14 but preventing the breast milk from spilling out of the vent 108, and more particularly, the hole 110. By way of example and not limitation, other venting systems known in the art are those described in U.S. Pat. Nos. 5,570,796 and 5,779,071. These and other venting systems incorporate the vent mechanism between the cap 98 and the container 14. Additionally, it is also contemplated that the hydrophobic filter 114 may be disposed at the hole 110. By doing so, air is still allowed to be introduced into the container 14 and breast milk is still prevented from spilling out of the container 14 through the hole 110 of the vent 108.

In the description of the system 10, a cylindrical container 14 is utilized. However, other container shapes and configurations are also contemplated. By way of example and not limitation, the container 14 may be a ventable nursing bottle or a collapsible bag without a vent. As a further alternative, a syringe body may be used in lieu of the container 14 and cap 98. The needle side of the syringe is disposed toward the bottom side of the system. The plunger is removed and the top side of the syringe body is opened to the atmosphere to allow the breast milk or nutritional fluid in the syringe body to drain out the bottom of the container through the syringe needle. A permeable material or hydrophobic material may cover the open top side of the syringe body to prevent particulate matter and contaminates from contaminating the breast milk.

The peristaltic pump 16 is operative to receive a section of the extension tube 106. In particular, the peristaltic pump has a groove 120 through which the extension tube 106 may be inserted. The section of the extension tube 106 inserted into the groove 120 and interacting with rollers of the peristaltic pump 16 may be more compliant compared to the remaining portions of the extension tube 106. When the extension tube 106 is inserted into the groove 120, rollers (not shown) of the peristaltic pump 16 successively squeeze the extension tube 106 to flow the breast milk through the extension tube 106 and the feeding tube 122. In this regard, the peristaltic pump 16 causes the breast milk to flow through the tube 106, 122 at a highly controlled rate. In operation, when the container 14 is disposed within the cooling unit 12, the output port 102 is disposed on the bottom of the container so that gravity can force all of the breast milk through the output port 102. The breast milk flows through the output port 102 and into the extension tube 106. The peristaltic pump 16 creates a vacuum to pump out the breast milk from the container 14. Moreover, the peristaltic pump is capable of pumping out all of the breast milk contained within the container through the output port 102 and out of the extension tube 106 and the feeding tube 122 including the fat content that might line the lumen of the tube. The breast milk contained within the extension tube 106 and the feeding tube 122 may also be fed to the preterm infant by pumping air behind the breast milk contained in the tubes 106, 122. Beneficially, the air is not fed to the neonate because the pump 16 may be stopped when all of the breast milk is pumped out of the tube or when a small amount of nutritional liquid is left in the feeding tube. A vent 108 formed in the cap 98 allows air to continue to enter into the container 14 and be introduced into the tubes 106, 122 to prevent a vacuum from forming at the end of the feeding cycle and to allow the pump to continue pumping all of the breast milk out of the container 14 and the tubes 106, 122. The flow rate of the breast milk through the extension tube 106 and the feeding tube 122 may be calculated based on the size (e.g., length and inner diameter) of the tubes 106, 122 and the speed of the peristaltic pump 16. The volume of breast milk in the extension tube 106 and feeding tube 122 may be calculated with this information and be used to time stoppage of the pump 16. It is also contemplated that the extension tube 106 and the feeding tube 122 may be formed as a single tube that serves the two functions described in relation to the extension tube 106 and the feeding tube 122.

To feed all of the breast milk in the container 14 to the preterm infant, the peristaltic pump 16 may continue to operate (i.e., pump) for a period of time as soon as a fluid level detector detects that the container 14 is empty. The fluid level detector may sense a level of the fluid in the container after start of the pump. When the container 14 is empty, the breast milk is located only in the tubes 106, 122. The continued operation of the pump 16 allows for feeding of the breast milk in the tubes 106, 122 to minimize waste of valuable breast milk. The pump 16 continues to operate for a period of time equal to the flow rate of breast milk through the tubes 106, 122 multiplied by the volume of the extension tube 106 and the feeding tube 122.

Referring now to FIG. 3, to detect a level of the breast milk in the container 14, a suitable fluid level detection device, such as a camera 124 that makes up a cameral vision system may be disposed adjacent the container 14 when the container 14 is disposed between first and second modules 22, 24 in the closed position. The camera 124 may be operative to detect the level of the breast milk contained within the container 14 so as to detect when the breast milk is emptied out of the container 14 during the feeding process. Lights 125 which may also form a part of the camera vision system may be disposed behind the container 14 to illuminate the back of the container 14 to help gauge the level of the breast milk still contained within the container 14 with the camera 124. The camera 124 is operative to send a signal to a controller of the peristaltic pump 16 so that the peristaltic pump 16 stops pumping after the period of time described above so that all of the breast milk contained in the tubes 106, 122 is pumped out and administered to the preterm infant or neonate. A typical flow rate for the peristaltic pump 16 and tubes 106, 122 combination is typically about 0.5 to 20 ml per minute.

Other fluid level sensors are also contemplated in lieu of the camera 124 and lights 125. By way of example and not limitation, LED or laser fluid level measurement systems are also contemplated for detecting the level of breast milk in the container 14 or for detecting when fluid is emptied out of the container 14. Additionally or alternatively, a rotary encoder on the motor of the peristaltic pump 16 may be used to calculate when the breast milk is depleted from the container 14. In particular, the user may enter the fluid volume of breast milk initially in the container 14 when loading the container 14 in the cooling unit 12. This information is entered into a controller of the system 10 which calculates the appropriate period of time the peristaltic pump 16 should operate to administer all of the breast milk. The controller is operative to time shut off of the peristaltic pump 16 to deliver all of the breast milk to the preterm infant and to prevent pumping air into the stomach of the preterm infant. In another embodiment, it is also contemplated that weight of the container 14 and the breast milk within the container 14 may be measured with a load cell to determine the remaining amount of breast milk in the container 14.

Other sensors are also contemplated that may be incorporated into the system 10 in order to assist in timing operation of the pump 16 in order to administer all of the breast milk in the container 14 yet not undesirably pump air into the preterm infant. By way of example and not limitation, a fluid sensor 126 may be disposed adjacent to the feeding tube 122 to detect when the last bit of breast milk is flowed through the feeding tube 122. The pump 16 may be shut off shortly thereafter in order to allow the last remaining amount of breast milk still trapped in the feeding tube 122 to be fed to the preterm infant. The amount of time that the pump 16 is allowed to continue running after the fluid sensor 126 detects an absence of fluid may be calculated based on the flow rate of the breast milk through the feeding tube 122 and a volume of breast milk still contained in the feeding tube 122 between the fluid sensor 126 and a proximal end of the tube 122. This information may be input into the controller of the system 10 with the keypad as discussed herein. The fluid sensor 126 may be placed at other locations on the feeding tube 122 and the extension tube 106. The fluid sensor 126 may be a laser or LED-based fluid sensor, camera imaging system or other suitable fluid sensors The warming unit 18 may be operative to heat the breast milk being administered to the preterm infant above room temperature, and more preferably up to about standard body temperature which is 98.6 F. The system 10 may be used in a neonatal intensive care unit environment. These types of environments are regulated to a room temperature between 72° F. to 76° F. with an air conditioning unit. The warming unit 18 may be identical to the structure described in U.S. Pat. No. 8,663,161 and Ser. No. 14/222,832, the entire contents of which are expressly incorporated herein by reference. The warming unit 18 may be controlled with a controller disposed within the body 20 of the system 10. The controller may be in electrical communication with the warming unit 18 by way of cable 130. Additionally, power may be supplied to a heating element in the warming unit 18 through the cable 130. The warming unit 18 may be disposed closely adjacent to the preterm infant so that after the breast milk is heated, the heated breast milk does not have to travel very far downstream of the warming unit 18 to the preterm infant. The reason is that oftentimes administration of breast milk to the preterm infant is a very slow process. The breast milk begins to cool down as soon as the breast milk exits the warming unit 18. By placing the warming unit 18 closely adjacent to the preterm infant so that only a short portion of the feeding tube 122 is exposed to the environment, one may mitigate excessive cooling down of the heated breast milk so that the preterm infant receives the milk at or close (±2° to 5° F.) to the standard body temperature.

The system 10 may also have a display 132 and keypad 134. It is also contemplated that the keypad 134 and display 132 may be incorporated into a touchpad. The keypad 134 and display 132 provide input and outputs for the user to communicate with the controller of the system 10. By utilizing the keyboard 134, the user may configure the controller and set various parameters such as total volume of breast milk to be administered to the preterm infant, time for infusion or feeding cycle, infusion or flow rate of the breast milk to be administered to the preterm infant, target temperature of the breast milk being fed to the preterm infant, upper and lower acceptable temperature ranges of the breast milk to be fed to the preterm infant and other factors necessary or important to the operation of the system 10. The keypad 134 may also be used to configure various alarms which may be visual (i.e. LEDs, informational text on the display 132) or auditory (i.e., bells, audible voices on a speaker of the system 10, warning sounds on the speaker of the system 10). The controller of the system 10 is operative to control the peristaltic pump 16, the warming unit 18, the cooling unit 12, the camera 124 or the fluid level indicator and other operational features of the system 10. The controller of the system 10 may also incorporate a memory function to provide medical professionals with a fast setup of the system 10. In particular, the medication professional may recall a prior setting for a particular preterm infant in the NICU when setting up a feeding cycle for the preterm infant so that the medical professional need not reenter the same information for subsequent feedings. The controller may be programmable so as to receive various inputs which control other parts of the system 10.

The system 10 may also have a speaker 136 for providing an audible response such as warnings, instructions and other useful information to the medical professional. Moreover, the system 10 may have one or more lights 138 that may also serve to provide a warning signal to the medical professional of a malfunction or error in operation. Additionally, the display 132 may serve the same function in warning the medical professional and providing instruction as to operation as well as an error in operation of the system 10.

The system 10 may also be network enabled. The system 10 may have a wireless antenna 140 for transmitting and/or receiving information and/or command signals from a remote location such as a nurse's station. In this regard, the system 10 may have one or more sensors and data collection devices that measure a temperature of the breast milk contained in the container 14, the flow rate of the breast milk to the neonate, entry and exit temperatures of the breast milk from the heater 18 and other important information of the system 10. This as well as other information may be transmitted to the remote location such as the nurse's station so that the nurse need not personally attend to the feeding of the neonate and may attend to other more critical tasks at hand unless a serious error occurs. In the event of a serious error, the wireless antenna 140 may also be operative to receive commands from the remote location to increase or decrease flow rate of the breast milk, increase or decrease exit temperature of the breast milk and control other aspects of the system 10. The same may also be accomplished by providing for a hardwired connection to the system with a network port 142 which connects the system 10 to the network of a hospital so that control of the system 10 at the remote location is possible.

The system 10 requires energy to power the thermoelectric cooler 66, the display 132, the keyboard 134, the pump 16, the warming unit 18 and other components such as the lights 138, the speaker 136 and the sensor 126. Power may be provided to the system 10 by plugging the system 10 into an electrical outlet with plug 144. Electricity is provided to power supply 146 which both provides power to the required components within the system 10 and also a backup rechargeable battery 148. The power supply 146 is operative to provide standard 110V AC power or DC electricity to the various components as needed. A battery receptacle 150 may hold the rechargeable battery 148 in place during use. However, in certain instances, it may be desirable to replace the backup battery 148 with a fresh recharged battery. In this instance, the backup battery 148 may be selectively removed from the battery receptacle 150. During operation, the electrical plug provides electricity to the system 10 and also charges the backup battery 148. In the event of a power outage, the backup battery 148 powers the system 10 until power is restored. In certain remote locations where electricity is not available, it may be desirable to carry multiple backup batteries which are switched out between feedings in order to utilize the system 10.

The system 10 may also include an agitation mechanism or system for stirring the breast milk contained in the container 14 during feeding. In particular, the agitation mechanism may include a stir bar which is disposable within the container 14. The stir bar may be inserted into the container 14 before sealing the container 14 with replaceable cap 98. The stir bar is rotatable with a rotating magnet device. The rotating magnet device may be incorporated into the cap 98 and activated when the pump 16 is activated. In this instance, when the pump is activated, the rotating magnet device is operable to rotate the stir bar in order to stir the breast milk during the feeding process. The stir bar may be shaped in the form of a rotary propeller. Other mechanisms for stirring or agitating the breast milk are also contemplated. By way of example and not limitation, it is also contemplated that a piezoelectric or ultrasonic vibration may be incorporated into the container 14 and/or cap 98.

As discussed above, the system 10 utilizes an extension tube 106 and a feeding tube 122. The extension tube 106 is fed through the peristaltic pump 16 and the warming unit 18. The feeding tube 122 is connected to the extension tube 106 so as to be in fluid communication therewith. The feeding tube 122 is designed to be inserted into the stomach of the neonate. Although the above description of the system 10 is in conjunction with two separate tubes 106, 122, it is also contemplated that a single tube may be used to connect to the output port 102 of the cap 98, be fed through the peristaltic pump 16, routed through the warming unit 18 and inserted into the stomach of the neonate.

The system 10 may also be configured to be mountable to an IV pole by way of clamp 152 where, for example the clamp is disposed about the IV pole and a knob 154 is tightened to clamp the system 10 to the IV pole. The system 10 may also be set on a tabletop.

In operation, the system 10 may be used to feed a preterm infant or neonate nutritional fluid such as a mother's breast milk, a donor mother's breast milk or a neonate nutritional formula. For breast milk whether it is the neonate's mothers or donor's breast milk, the breast milk is preferably pumped into the container 14 then fed to the neonate immediately after pumping. In other cases, the breast milk is stored in a refrigerated state for later use. Refrigeration mitigates unwanted bacteria growth in the breast milk. The breast milk is typically stored at a temperature of about 39° F. The system 10 may incorporate commonly used containers 14 used in common breast pumps in the market. However, it is also contemplated that the system 10 may be designed to receive specially designed containers 14.

A preterm infant typically is unable to orally consume nutritional fluid (i.e., breast milk or neonate nutritional formula) through the mouth with a bottle. As such, preterm infants require assistance in receiving nutritional fluid by placing a feeding tube 122 through the infant's mouth or nose until a distal end of the feeding tube 122 reaches the infant's stomach. The system 10 may be utilized to feed preterm infants breast milk in a way that mitigates unwanted bacterial growth, retains the nutritional and fat content of breast milk, provides the nutritional fluid to the preterm infant at the optimal temperature (i.e., standard body temperature) and efficiently feeds the infant at a preselected time or interval, if desired, so that the medical professional may set up the system 10 for feeding at a later time and attend to more critical tasks at hand.

To utilize the system 10, the system 10 may be set up on a tabletop or attached to an IV pole with clamp 152 in close proximity to the preterm infant. A container 14 is removed from the refrigerator and prepared for feeding the breast milk in the container 14 to the preterm infant. The container 14 is preferably the same container that the neonate's mother or the donor mother used to pump her breast milk. Utilizing the same container 14 mitigates possible reduction of the fat content within the breast milk. Although it is preferable to use the same container 14, it is also sometimes necessary to transfer the breast milk from one container 14 to another such as when the feeding volume does not match stored volume or fortification in specific volume increments is necessary. To prepare the container 14 for feeding, the cap 94 is removed and the ventable cap 98 is placed on the container 14. The extension tube 106 is connected to the output port 102 and the feeding tube 122 is connected to the extension tube 106. Thereafter, the tubes 106, 122 are primed with the breast milk from the container 14 by inverting the container 14 in the orientation shown in FIG. 1. Once the tubes 106, 122 are primed with the breast milk, the feeding tube 122 may be inserted through the preterm infant's mouth until a distal end is disposed or positioned within the infant's stomach.

The medical professional may power on the system 10 with power switch 160 which supplies power to the various components of the system 10. The medical professional operates a keyboard 134 to traverse the first and second modules 22, 24 to the opened position with the motor 30. Alternatively, the first and second modules 22, 24 may be traversed to the opened position with a hand crank. Once the first and second modules 22, 24 are in the opened position, the medical professional inverts the container 14 and inserts the container 14 between the first and second cooling modules 22, 24. While holding the container 14 between the first and second modules, the medical professional then operates the keyboard 134 in order to traverse the first and second modules 22, 24 to the closed position. In the closed position, the first and second cooling modules 22, 24 grip the container 14 to hold the container 14 in place.

The medical professional may then open the warming unit 18 in order to feed the extension tube 106 through the warming unit 18. At this point, the peristaltic pump 16 and the warming unit 18 are nonoperational. Moreover, fluid is not being flowed into the preterm infant's stomach.

Based on the preterm infant's condition and status, the medical professional may configure the controller of the system 10 in order to start the peristaltic pump 16 and the warming unit 18 at a later time. This is known as delayed start. For example, if the feeding time is at 1:00 PM, the medical professional may set up the system 10 at 12:30 and set the feeding cycle to start at 1:00 PM. The medical professional through the keyboard 134 also programs the system 10 with the total volume of breast milk to be fed to the preterm infant and the infusion rate or flow rate of the breast milk to be flowed to the preterm infant. By default, the warming unit 18 warms up the breast milk flowing through the extension tube 106 to a temperature of about 98.6° F. (+/−5°, and more preferably +/−2° F.) for the feeding cycle. It is also contemplated that the breast milk may be heated to a temperature above or below 98.6° F. but the medical professional must alter such setting with the keyboard 134. Additionally, the medical professional may set an acceptable temperature range of the breast milk such as +/−2° F. from the target temperature (i.e., 98.6° F.). A sensor may be used to track the temperature of the breast milk and send a signal to the controller to trigger an alarm when the temperature of the breast milk exceeds the range of the target temperature. It is also contemplated that the medical professional may immediately start the feeding cycle.

Additionally, the medical professional may set the target temperature of the breast milk in the container 14. In particular, as the system 10 waits for the start of the feeding cycle, it is beneficial to maintain the breast milk in the container 14 in a cooled state or a temperature below room temperature. The purpose is to mitigate unwanted bacterial growth and maintain fat content in the breast milk. To accomplish this, a suitable thermoelectric cooler, such as a Peltier module 66 of the first and second modules 22, 24 is activated. A noncontact temperature sensor may be utilized to gauge the temperature of the breast milk within the container 14 and provide feedback to the controller which in turn increases or decreases the Peltier effect of the thermally electric cooler 66 to maintain the breast milk at the target temperature. Additionally, if the temperature of the breast milk deviates from the target temperature, an alert, such as an alarm may be generated in order to alert a nurse at a remote location to attend to the situation.

When the feeding cycle starts, the system 10 powers the warming unit 18 and the peristaltic pump 16. Preferably, the system 10 powers the warming unit 18 prior to powering the peristaltic pump 16 in order to minimize the amount of cold breast milk being fed into the preterm infant. Once the warming unit 18 reaches the target temperature, the peristaltic pump 16 is powered up in order to begin flowing breast milk through the tubes 106, 122 and into the preterm infant. The breast milk is drawn through the bottom of the inverted container 14 and can draw all of the breast milk out of the container 14. Given that breast milk is the optimal type of nutritional fluid for the preterm infant, it is crucial to provide as much of the optimal type of nutritional fluid to the preterm infant who may already be struggling for life and may need all of the nutrients and immunological benefits of breast milk.

As the feeding cycle progresses, the level of breast milk in the container 14 decreases. The level of the breast milk in the container may be monitored with the camera 124 and if needed, the lights 125 may be turned on to illuminate the breast milk within the container 14 to assist the camera 124 in determining the level of the breast milk in the container 14. When the camera 124 detects that all of the breast milk is depleted from the container 14, a controller in the system may set a timer for stopping operation of the peristaltic pump 16 right before air is fed to the neonate. The peristaltic pump 16 delivers the breast milk in a highly controlled rate. As such, since the volume of the breast milk in the tubes 106, 122 and the flow rate through the tubes 106, 122 are known, the controller turns off the peristaltic pump 16 when the volume of breast milk in the tubes 106, 122 has been completely fed to the preterm infant right before air is introduced into the neonate. In this manner, all of the breast milk is fed to the preterm infant without pumping air into the preterm infant.

Other means of stopping the peristaltic pump 16 at the appropriate time to deliver all of the breast milk to the preterm infant while not introducing air to the preterm infant are also contemplated. By way of example and not limitation, a fluid sensor 126 may be located on various portions of the tube 106, 122. By way of example and not limitation, the fluid sensor 126 may be positioned near the preterm infant's mouth on the feeding tube 122. Once the fluid sensor 126 detects an absence of breast milk or nutritional fluid in the feeding tube 122, the peristaltic pump 16 may be immediately stopped or stopped shortly thereafter.

In certain instances, the preterm infant may not consume the entire fluid volume of breast milk contained in the container 14. By way of example and not limitation, the preterm infant may consume one half of the volume of breast milk in the container 14. As such, the breast milk in the container 14 may be utilized for two feeding cycles. In this regard, after the first feeding cycle, the peristaltic pump 16 stops. The peristaltic pump 16 is stopped when the feeding volume set by the medical professional has been met. Additionally, the warming unit 18 is turned off to prevent overheating of the breast milk contained in the tube 106 routed in the warming unit 18. The cooling unit 12 maintains the breast milk in the container 14 at the refrigerated temperature to mitigate bacterial growth so that the medical professional need not immediately attend to the preterm infant. When the next feeding cycle is desired, the tubes 116 and 122 can be replaced with sterile replacement tubes and the warming unit 18 is powered back on until it reaches its target temperature. The peristaltic pump 16 begins to pump breast milk through the tubes 116, 122 and into the preterm infant. All of the fluid is then fed to the preterm infant by emptying out the breast milk from the container 14 and feeding all of the breast milk contained in the tube 106, 122 to the preterm infant as discussed above.

During operation, the warming unit 18, peristaltic pump 16 or the cooling unit 12 may fail. In this regard, the cooling unit 12 may fail to cool down the breast milk in the container 14. In this regard, the noncontact liquid temperature sensor may trigger one of the visual or audible alarms of the system 10 and also send a signal through the wireless antenna 140 or the wired port 142 to a remote location (i.e., nurse's station) so that the medical professional at the remote location may quickly attend to the system 10.

Before, during and after the feeding cycle, the cooling unit 12 maintains the breast milk contained in the container 14 in a cold state. In this regard, condensation may form in or around the cooling unit 12 and the container 14. To mitigate condensation, a sponge may be disposed about the container 14 or air may be blown over such areas.

Additionally, during the feeding cycle, the agitation mechanism may be triggered to stir the breast milk within the container 14.

During the feeding cycle, the display 132 may show various parameters such as infusion rate, duration of the feeding cycle, remaining duration of the feeding cycle, temperature of the breast milk in the container 14, temperature of the warming unit 18 and any other relevant information.

The various aspects of the system 10 may be utilized to provide assisted feeding to neonates but may be especially beneficial to feed patients such as preterm infants that may already be struggling for life. For these patients, nutrition should be provided on time and regularly to provide the best chance of survival. However, the system 10 may also be used to provide assisted liquid feeding to children and adults that might not be able to orally intake food but must consume nutrition directly into the stomach.

The above description is given by way of example, and not limitation. Given the above disclosure, one skilled in the art could devise variations that are within the scope and spirit of the invention disclosed herein, including various ways of incorporating the warming unit into the system. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A system for feeding a neonate, the system comprising:
a body;
a holding mechanism coupled to the body and moveable relative thereto for facilitating engagement with a container to position the for positioning a container in an inverted position so that breast milk contained within the container flows out downward from the container;
a pump for pumping the breast milk contained within the container;
a sensor for determining an amount of breast milk remaining in at least one of the container and a tube connectable to the container, the tube being disposable within the neonate; and
a controller for controlling the pump, the controller operative to regulate a speed of the pump to provide a consistent flow rate of the breast milk to the neonate and to shut off the pump after determining the amount of breast milk remaining in the container or the tube or both so that all of the breast milk in the container is fed to the neonate and without delivering air into the neonate.

2. The system of claim 1 further comprising a cooling unit coupled to the body and including the holding mechanism, the cooling unit being operative to cool the breast milk contained in the container for mitigating bacterial growth before and during feeding.

3. The system of claim 2, wherein the cooling unit includes a thermoelectric cooler.

4. The system of claim 3, wherein the cooling unit further includes at least one fan to promote airflow therein.

5. The system of claim 3, further comprising a conduit for directly fluid flow toward the cooling unit to mitigate condensation.

6. The system of claim 1 wherein the pump is a peristaltic pump for flushing all of the breast milk out of the tube.

7. The system of claim 1, wherein the holding mechanism includes a pair of opposed surfaces moveable relative to the body to transition the holding mechanism between a closed position and an open position, the pair of surfaces moving toward each other to transition the holding mechanism from the open position toward the closed position.

8. The system of claim 7, wherein each of the opposed surfaces includes an arcuate portion.

9. The system of claim 7, further comprising a rotation axle coupled to the pair of opposed surfaces such that rotation of the rotation axle facilitates translation of the pair of opposed surfaces between the closed and open positions.

10. The system of claim 9, further comprising a motor coupled to the rotation axle to facilitate rotation of the rotation axle.

11. A system for feeding a neonate, the system comprising:
a body;
a holding mechanism coupled to the body and moveable relative thereto for facilitating engagement with a container to position the container containing nutritional fluid for the neonate;
a pump for pumping the nutritional fluid contained within the container;
a controller operative to start and stop operation of the pump for starting and stopping flow of nutritional fluid in a tube connected in fluid communication with the container, the tube being disposed within the neonate to deliver the nutritional fluid to the neonate; and
wherein the controller is operative to delay changing the pump from an off to an on condition until a user selected period of time, based on parameters set by a medical professional, has elapsed.

12. The system of claim 11 further comprising a cooling unit for cooling the nutritional fluid to a temperature 76 degrees Fahrenheit or below, the controller operative to start the cooling unit during the period of time while waiting for the delay start of the pump.

13. The system of claim 12, wherein the cooling unit includes a thermoelectric cooler.

14. The system of claim 13, wherein the cooling unit further includes at least one fan to promote airflow therein.

15. The system of claim 14, further comprising a conduit for directly fluid flow toward the cooling unit to mitigate condensation.

16. The system of claim 11, wherein the holding mechanism includes a pair of opposed surfaces moveable relative to the body to transition the holding mechanism between a closed position and an open position, the pair of surfaces moving toward each other to transition the holding mechanism from the open position toward the closed position.

17. The system of claim 16, wherein each of the opposed surfaces includes an arcuate portion.

18. The system of claim 16, further comprising a rotation axle coupled to the pair of opposed surfaces such that rotation of the rotation axle facilitates translation of the pair of opposed surfaces between the closed and open positions.

19. The system of claim 18, further comprising a motor coupled to the rotation axle to facilitate rotation of the rotation axle.

20. A system for feeding a neonate, the system comprising:
a body;
a cooling unit coupled to the body and engageable with a container including neonatal feeding fluid for cooling the container, the cooling unit including a pair of modules sized and structured to be cooperatively engageable with the container, the pair of modules being moveable relative to the body for facilitating engagement with the container;
a pump for pumping the neonatal feeding fluid from within the container when the container is engaged with the cooling unit;

a sensor for determining an amount of neonatal fluid remaining in the container when the container is engaged with the cooling unit; and a controller for controlling the pump, the controller operative to regulate a speed of the pump to provide a prescribed flow rate of the neonatal feeding fluid to the neonate and to shut off the pump after determining the amount of neonatal feeding fluid remaining in the container is below a prescribed level.

* * * * *